United States Patent
Gebhardt et al.

(10) Patent No.: US 8,017,556 B2
(45) Date of Patent: Sep. 13, 2011

(54) CRYSTALLINE FORM OF [3-(4,5-DIHYDRO-3-ISOXAZOLYL)-2-METHYL-4-(METHYLSULFONYL)PHENYL]-(5-HYDROXY-1-METHYL-1H-PYRAZOL-4-YL)METHANONE

(75) Inventors: Joachim Gebhardt, Wachenheim (DE); Peter Erk, Frankenthal (DE); Heidi Emilia Saxell, Carlsberg (DE); Thomas Kroehl, Schriesheim (DE); Matthias Bratz, Maxdorf (DE)

(73) Assignee: BASF SE, Ludwigshafen (DE)

( * ) Notice: Subject to any disclaimer, the term of this patent is extended or adjusted under 35 U.S.C. 154(b) by 73 days.

(21) Appl. No.: 12/667,120

(22) PCT Filed: Jul. 4, 2008

(86) PCT No.: PCT/EP2008/058712
§ 371 (c)(1),
(2), (4) Date: Dec. 29, 2009

(87) PCT Pub. No.: WO2009/007329
PCT Pub. Date: Jan. 15, 2009

(65) Prior Publication Data
US 2010/0197502 A1    Aug. 5, 2010

(30) Foreign Application Priority Data
Jul. 6, 2007   (EP) .................................. 07111981

(51) Int. Cl.
*A01N 43/80* (2006.01)
*A01P 13/00* (2006.01)
*C07D 413/10* (2006.01)

(52) U.S. Cl. ........................ 504/271; 548/240
(58) Field of Classification Search ................... 504/271; 548/240
See application file for complete search history.

(56) References Cited

U.S. PATENT DOCUMENTS

| 6,469,176 | B1  | 10/2002 | von Deyn et al. |
| 6,525,204 | B1  | 2/2003  | Rheinheimer et al. |
| 6,534,444 | B1  | 3/2003  | Sievernich et al. |
| 7,232,792 | B2* | 6/2007  | von Deyn et al. ............. 504/266 |
| 2010/0160165 | A1 | 6/2010 | Bratz et al. |
| 2010/0227763 | A1 | 9/2010 | Krapp et al. |

FOREIGN PATENT DOCUMENTS

| CA | 2 278 331 | 7/1998 |
| WO | WO 98/31681 | 7/1998 |
| WO | WO 99/58509 | 11/1999 |

OTHER PUBLICATIONS

International Search Report completed Oct. 23, 2008, in International Application No. PCT/EP2008/058712, filed Jul. 4, 2008.
International Preliminary Report on Patentability dated Jan. 12, 2010, from corresponding International Application No. PCT/EP2008/058712, filed Jul. 4, 2008.
Schönhammer, A., et al., "Topramezone—ein neuer Herbizidwirkstoff sur hochselektiven Hirse- and Unkraoutbekämpfung in Mais", Journal of Plant Diseases and Protection, 2006, p. 1023-1031.

* cited by examiner

*Primary Examiner* — Yong Chu
(74) *Attorney, Agent, or Firm* — Brinks Hofer Gilson & Lione

(57) ABSTRACT

The present invention relates to crystalline forms of [3-(4,5-dihydro-3-isoxazolyl)-2-methyl-4-(methylsulfonyl)phenyl]-(5-hydroxy-1-methyl-1 H-pyrazol-4-yl)methanone, which is also known under the common name topramezone. The invention also relates to a process for the preparation of these crystalline forms and formulations for plant protection which comprise one of these crystalline forms of topramezone.

9 Claims, 6 Drawing Sheets

CRYSTALLINE FORM OF [3-(4,5-DIHYDRO-3-ISOXAZOLYL)-2-METHYL-4-(METHYLSULFONYL)PHENYL]-(5-HYDROXY-1-METHYL-1H-PYRAZOL-4-YL)METHANONE

This application is a National Stage application of International Application No. PCT/EP2008/058712 filed Jul. 4, 2008, the entire contents of which is hereby incorporated herein by reference. This application also claims the benefit under 35 U.S.C. §119 of European Patent Application No. 07111981.2, filed Jul. 6, 2007, the entire contents of which is hereby incorporated herein by reference.

The present invention relates to crystalline forms of [3-(4,5-dihydro-3-isoxazolyI)-2-methyl-4-(methylsulfonyl)phenyl]-(5-hydroxy-1-methyl-1H-pyrazol-4-yl)methanone, which is also known under the common name topramezone. The invention also relates to a process for the preparation of these crystalline forms and formulations for plant protection which contain one of these crystalline forms of topramezone.

Topramezone is the herbicidal active substance of the formula I and also the tautomer of the formula I'.

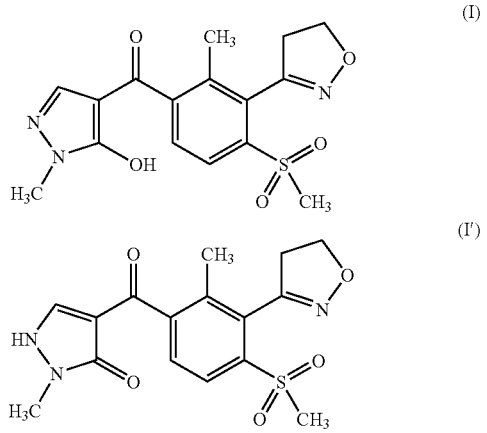

Topramezone and a general procedure for its preparation are known from WO 98/31681 and WO99/58509.

For the preparation of active substances on the industrial scale but also for the formulation of active substances, the knowledge of the possible existence of crystalline modifications (also known as crystalline forms) or of solvates of the active substance in question, the knowledge of the specific properties of such modifications and solvates and of methods for their preparation is in many cases of decisive importance. A number of active substances can exist in different crystalline modifications but also in amorphous ones. These cases are referred to as polymorphism. A polymorph is a solid, crystalline phase of a compound, which is characterized by a defined, uniform, packing and arrangement of the molecules in the solid substance.

Different modifications of one and the same active substance can sometimes display different properties, for example differences in the following properties: solubility, vapor pressure, dissolution rate, stability to phase conversion into another modification, stability during milling, suspension stability, optical and mechanical properties, hygroscopicity, crystal shape and size, filterability density, melting point, stability to decomposition, color and sometimes also chemical reactivity or biological activity.

The applicant's own attempts to convert topramezone into a crystalline solid by crystallization at first resulted in complex mixtures of different crystal modifications. The stability of formulations prepared from these was not in all cases satisfactory.

It has now surprisingly been found that by defined processes a previously unknown crystalline, stable modification of topramezone, which does not display the disadvantages of the other solid forms of topramezone, is obtained in high purity. This modification is also referred to hereinafter as form I. In addition a further four crystalline forms of topramezone and three crystalline solvent solvates of topramezone, which however had lower stability, were found. These forms are referred to hereinafter as form II, form III, form IV, form VIII, form V-S, form VI-S and form VII-S.

Moreover, the crystalline form I according to the invention is easier to handle than other solid forms of topramezone, since it is obtained in the form of discrete crystals or crystallites during its preparation. Unlike the acicular crystals of the other polymorphs of topramezone, form I is obtained in compact, generally block-shaped crystals which are easier to filter. Compared to other solid forms, form I displays increased stability with regard to conversion into another form. The stability of formulations which comprise topramezone in form I is also markedly higher than the stability of formulations which comprise other solid forms of topramezone.

The term "pure form I" used here and below should be understood to mean that the content of the form I modification, based on the total quantity of topramezone in the solid or in the formulation, is at least 90% by weight and in particular at least 95% by weight.

Accordingly, a first object of the present invention relates to the crystalline form I of topramezone. Also an object is a topramezone which at least 90% by weight, in particular at least 95% by weight, consists of the crystalline form I.

The form I according to the invention can be identified by X-ray powder diffractometry on the basis of its diffraction diagram. Thus, an X-ray powder diffractogram recorded at 30° C. using Cu-Kα radiation (1.54178 Å) displays at least 5, often at least 6, in particular at least 7, and especially all of the reflections stated in the following Table 1 as 2θ values, and as interplanar spacings d:

TABLE 1

| 2θ | d [Å] |
|---|---|
| 7.7 ± 0.2 | 11.46 ± 0.05 |
| 10.3 ± 0.2 | 8.58 ± 0.05 |
| 12.7 ± 0.2 | 6.96 ± 0.05 |
| 13.8 ± 0.2 | 6.42 ± 0.04 |
| 16.9 ± 0.2 | 5.24 ± 0.03 |
| 18.8 ± 0.2 | 4.72 ± 0.03 |
| 20.7 ± 0.2 | 4.28 ± 0.02 |
| 22.2 ± 0.2 | 4.00 ± 0.02 |
| 28.0 ± 0.2 | 3.19 ± 0.02 |
| 31.4 ± 0.2 | 2.81 ± 0.02 |

Studies on single crystals of form I show that the basic crystal structure is monoclinic. The unit cell has the space group P2(1)/c. The characteristic data of the crystal structure of form I (determined at 20° C.) are summarized in Table 2.

TABLE 2

Crystallographic properties of form I

| Parameter | Form I |
| --- | --- |
| Class | monoclinic |
| Space group | P2(1)/c |
| a | 11.477(4) Å |
| b | 12.840(4) Å |
| c | 11.523(5) Å |
| α | 90° |
| β | 92.094(9)° |
| γ | 90° |
| Volume | 1697.0(8) Å$^3$ |
| Z | 4 |
| Density (calculated) | 1.42 g/cm$^3$ |
| R$^1$; ωR$^2$ | 0.09, 0.23 |
| Wavelength | 1.54178 Å | a, b, c = edge length of the unit cell
α, β, γ = angles of the unit cell
Z = number of molecules in the unit cell Form I displays a thermogram with a characteristic melting peak. The melting point, determined as the start of the melting peak (onset), typically lies in the range from 218 to 221° C. The latent heat of fusion is about 126 J/g. The values stated here are based on values determined by differential calorimetry (Differential Scanning Calorimetry: DSC, open aluminum crucible, heating rate 10 K/min).

The preparation of the form I of topramezone according to the invention is effected by crystallization from a solution of topramezone in a suitable organic solvent. Suitable solvents for the crystallization of form I are $C_1$-$C_4$ alkanols such as methanol, ethanol or isopropanol, and also $C_2$-$C_4$ alkanediols such as glycol, and also acetone and mixtures thereof with water.

For this, in a first step i) a solution of topramezone in one of the aforesaid organic solvents is prepared and then in a second step ii) a crystallization of the topramezone is effected.

The concentration of topramezone in the solution used for the crystallization naturally depends on the nature of the solvent and the solution temperature and often lies in the range from 10 to 400 g/L. Suitable conditions can be determined by the person skilled in the art by routine experiments.

Preferably, the solution used for the crystallization comprises topramezone at a chemical purity of at least 85%, often at least 90%, in particular at least 95%, i.e. the content of organic impurities which are not organic solvents makes up not more than 15% by weight, often not more than 10% by weight and in particular not more than 5% by weight, based on the topramezone present dissolved in the solvent.

The solution used for the crystallization is preferably essentially free from solvents other than those named. In this context, "essentially free" means that the concentration of other solvents in the topramezone-containing solution does not exceed 10% by weight, often 5% by weight, based on the total quantity of solvent.

The solution of topramezone can for example be prepared by the following methods:
(1) dissolution of topramezone, preferably a form other than form I, in one of the aforesaid organic solvents, or
(2) preparation of topramezone by a chemical reaction and transfer of the reaction mixture, if appropriate after removal of reagents and/or side-products, in an organic solvent suitable according to the invention.

For the preparation of the solution by dissolution of topramezone essentially any known form of topramezone can be used. Often amorphous topramezone or a mixture of different crystalline modifications or a mixture of amorphous and crystalline topramezone will be used. Also suitable are crystalline forms of topramezone and mixtures thereof, e.g. the forms II, III, IV, V-S, VI-S or VII-S described below, and mixtures of these forms.

The dissolution of the topramezone usually takes place at temperatures in the range from 20 to 120° C. In a preferred embodiment of the invention, the dissolution of topramezone takes place at increased temperature, in particular at least 50° C., but naturally the temperature used for the dissolution will not exceed the boiling point of the solvent. Often the dissolution takes place at temperatures in the range from 50 to 120° C.

The solution of topramezone can also be prepared by transferring a reaction mixture obtained by a chemical reaction, which comprises the topramezone, if appropriate after removal of reagents and/or side-products, into an organic solvent suitable according to the invention. Here the procedure can be used of performing the reaction in an organic solvent or solvent mixture, which at least partially, preferably at least 50% by weight consists of a solvent suitable for the crystallization and, if necessary, performing a workup, wherein excess reagents and any catalysts present, and any unsuitable solvent present, e.g. water and/or methanol, are removed. The preparation of a solution of topramezone by chemical reaction of a suitable precursor of topramezone can be effected by analogy to the methods which are described in the state of the art described at the outset, to which reference is hereby made in its entirety.

The crystallization of form I of topramezone can be effected in the following manner, for example
  by cooling of the solution which comprises the dissolved topramezone,
  by concentration of the solution which comprises the dissolved topramezone, or
  by a combination of the aforesaid measures.

The crystallization is as a rule carried out until at least 80% by weight, preferably at least 90% by weight, of the topramezone used crystallizes out.

The crystallization of form I can be promoted or accelerated by seeding with seed crystals of form I, for example by adding seed crystals of form I before or during the crystallization.

If seed crystals are added during the crystallization, the quantity thereof is typically 0.001 to 10% by weight, often 0.005 to 5% by weight, in particular 0.01 to 1% by weight and especially 0.05 to 0.5% by weight, based on the dissolved topramezone.

If the crystallization is carried out in the presence of seed crystals of form I, these are preferably only added at a temperature at which the saturation concentration of topramezone in the solvent in question has been reached, i.e. at or below that temperature at which the dissolved quantity of topramezone in the solvent in question forms a saturated solution. The temperature dependence of the saturation concentration in a solvent can be determined in routine experiments by the person skilled in the art.

Alternatively, the form I of topramezone can be prepared by suspending topramezone in a $C_1$-$C_4$ alkanol or $C_2$-$C_4$ alkanediol or in a mixture of $C_1$-$C_4$ alkanol or $C_2$-$C_4$ alkanediol with water and agitating the suspended material in the suspension, e.g. by stirring. The agitation is preferably effected over a prolonged period, e.g. at least 2 hrs, e.g. 2 hrs to 6 days, in particular 4 hrs to 72 hrs.

If a mixture of $C_1$-$C_4$ alkanol or $C_2$-$C_4$ alkanediol with water is used, the quantity ratio of alkanol or alkanediol to water is selected such that topramezone is present not completely dissolved. The volume ratio alkanol: water or alkanediol: water preferably lies in the range from 1:20 to 10:1.

The suspending of the topramezone usually takes place at temperatures in the range from 20 to 120° C. If appropriate, the suspending can be carried out at increased temperature, in order to accelerate the conversion. In particular, the topramezon will be suspended for at least a certain period at increased temperature, in particular at least 50° C., but the temperature used will naturally not exceed the boiling point of the solvent or solvent-water mixture. Often the suspending is effected for a time at temperatures in the range from 50 to 140° C. Preferably before the separation of the mother liquor the suspension is cooled to a temperature below 30° C., for example to a temperature in the range from 5 to 30° C. and/or the suspension is concentrated. Preferably, the conditions are selected such that during the separation of the mother liquor, less than 20% by weight, preferably less than 10% by weight, of the topramezone used remains dissolved in the mother liquor.

The isolation of the form I from the crystallization product, i.e. the separation of the form I from the mother liquor, is achieved by normal techniques for the separation of solid components from liquids, e.g. by filtration, centrifugation or by decantation. As a rule, the isolated solid will be washed, for example with the solvent used for the crystallization, with water or with a mixture of the organic solvent used for the crystallization with water. The washing can be effected in one or more steps, the washing often being with water in the last step. The washing is typically effected at temperatures below 30° C., often below 25° C. and in particular below 20° C., in order to keep the loss of valuable product as low as possible. Next, the form I can be dried and then fed into further processing. Often, however, the moist active substance obtained after washing, in particular an active substance moist with water, will be fed directly into the further processing.

For suspending, a topramezone is preferably used which has a chemical purity of at least 85%, often at least 90%, in particular at least 95%, i.e. the content of organic impurities which are not organic solvent makes up not more than 15% by weight, often not more than 10% by weight and in particular not more than 5% by weight, based on the suspended topramezone present.

By the process according to the invention, the form I is obtained with a topramezone content of as a rule at least 90% by weight, often 94% by weight, in particular at least 96% by weight. The content of form I, based on the total quantity of topramezone is typically at least 90% and often at least 95% and especially at least 97%.

The preparation of the [3-(4,5-dihydro-3-isoxazolyl)-2-methyl-4-(methyl-sulfonyl)-phenyl]-(5-hydroxy-1-methyl-1H-pyrazol-4-yl)methanone used as starting material for the preparation of the form I can for example be effected by the process described in WO 99/58509 (e.g. according to Example 8 or 9), to which reference is hereby made in its entirety.

During the studies on crystalline modifications of topramezone a further form II was also identified. This is in particular a crystalline form of topramezone, which at least 90% by weight, in particular at least 95% by weight, consists of the crystalline form II.

The form II can be identified by X-ray powder diffractometry on the basis of its diffraction diagram. Thus, an X-ray powder diffractogram recorded at 30° C. using Cu-Kα radiation (1.54178 Å) displays at least 5, often at least 6, in particular at least 7 and especially all of the reflections stated in the following Table 3 as 2θ values, and as interplanar spacings d:

TABLE 3

| 2θ | d [Å] |
|---|---|
| 7.8 ± 0.2 | 11.29 ± 0.07 |
| 8.6 ± 0.2 | 10.33 ± 0.05 |
| 12.4 ± 0.2 | 7.10 ± 0.05 |
| 13.8 ± 0.2 | 6.40 ± 0.04 |
| 14.7 ± 0.2 | 6.01 ± 0.03 |
| 15.7 ± 0.2 | 5.65 ± 0.03 |
| 19.3 ± 0.2 | 4.59 ± 0.02 |
| 22.2 ± 0.2 | 4.00 ± 0.02 |
| 30.4 ± 0.2 | 3.69 ± 0.02 |

Studies on single crystals of form II show that the basic crystal structure is triclinic. The unit cell has the space group P-1. The characteristic data of the crystal structure of form II (determined at −173° C.) are summarized in Table 4.

TABLE 4

| Crystallographic properties of II | |
|---|---|
| Parameter | Form II |
| Class | triclinic |
| Space group | P-1 |
| a | 5.620(2) Å |
| b | 12.097(3) Å |
| c | 23.921(5) Å |
| α | 94.63(1)° |
| β | 90.61(2)° |
| γ | 98.28(2)° |
| Volume | 1603.7(6) Å$^3$ |
| Z | 4 |
| Density (calculated) | 1.51 g/cm$^3$ |
| R$^1$; ωR$^2$ | 0.084, 0.129 |
| Wavelength | 1.54178 Å | a, b, c = edge length of the unit cell
α, β, γ = angles of the unit cell
Z = number of molecules in the unit cell Form II displays a thermogram with a characteristic melting peak. The melting point, determined as the start of the melting peak (onset), typically lies in the range from 222 to 223° C. The latent heat of fusion is about 110 J/g. The values stated here are based on values determined by differential calorimetry (Differential Scanning Calorimetry: DSC, open aluminum crucible, heating rate 10 K/min).

The preparation of the form II of topramezone is effected by crystallization from a solution of topramezone in an aromatic solvent or a $C_5$-$C_8$ ketone at temperatures below 60° C., in particular at temperatures in the range from 10 to 50° C.

Examples of aromatic solvents are benzene, alkylbenzenes such as toluene, xylenes, mesitylene, cumene, etc., chlorobenzene, 1,2-dichlorobenzene, 1,3-dichlorobenzene, 1,4-dichlorobenzene and dichlorobenzene mixtures, anisole and acetophenone. Examples of $C_5$-$C_8$ ketones are acyclic ketones with 5 to 8 carbon atoms such as diethyl ketone (3-pentanone), methyl isobutyl ketone (4-methyl-pentan-2-one) and cyclic ketones with 5 to 8 C atoms such as cyclopentanone, cyclohexanone etc.

For this, in a first step i) a solution of topramezone in the desired solvent is prepared and then in a second step ii) a crystallization of topramezone is effected at temperatures below 60° C., in particular at temperatures in the range from 10 to 50° C. For the dissolution, the mixture of topramezone and the desired solvent can be heated to temperatures above the stated temperatures. It is essential that at a temperature of 60° C. no crystallization has yet started and that the crystallization only starts at temperatures below 60° C.

The crystallization of the form II of topramezone can be effected in the following manner, for example
- by cooling of the solution which comprises the dissolved topramezone to a temperature below 60° C.,
- by concentration of the solution which comprises the dissolved topramezone at a temperature below 60° C., or
- by a combination of the aforesaid measures.

Preferably, the crystallization is effected by concentration at temperatures in the stated temperature range.

The concentration of topramezone in the solution used for the crystallization often lies in the range from 10 to 300 g/L.

Preferably, the solution used for the crystallization of form II comprises topramezone at a purity of at least 85%, often at least 90%, in particular at least 95%, i.e. the content of organic impurities which are not organic solvent makes up not more than 15% by weight, often not more than 10% by weight and in particular not more than 5% by weight, based on the topramezone present dissolved in the solution.

The solution used for the crystallization is preferably essentially free from solvents other than aromatic solvents and $C_5$-$C_8$ ketones. In this context, "essentially free" means that the concentration of solvents including water which are other than aromatic solvents or a $C_5$-$C_8$ ketone in the topramezone-containing solution does not exceed 10% by weight and often 5% by weight, based on the total quantity of solvent.

For the preparation of the solution, essentially any known form of topramezone can be used. Often amorphous topramezone or a mixture of different crystalline modifications or a mixture of amorphous and crystalline topramezone will be used. Also suitable are crystalline forms of topramezone and mixtures thereof, e.g. the form I according to the invention, previously described and the form III, likewise described here, and the forms IV, V-S, VI-S or VII-S and mixtures of these forms.

The crystallization of form II can be promoted or accelerated by seeding with seed crystals of form II, for example by adding seed crystals of form II before or during the crystallization.

If seed crystals are added during the crystallization, the quantity thereof is typically 0.001 to 10% by weight, often 0.005 to 5% by weight, in particular 0.01 to 1% by weight and especially 0.05 to 0.5% by weight, based on the dissolved topramezone. If the crystallization is carried out in the presence of seed crystals of form II, these are preferably only added at a temperature at which the saturation concentration of topramezone in the solvent in question has been reached, i.e. at or below that temperature at which the dissolved quantity of topramezone in the solvent in question forms a saturated solution. The temperature dependence of the saturation concentration in a solvent can be determined in routine experiments by the person skilled in the art.

The isolation of the form II from the crystallization product, i.e. the separation of the form II from the mother liquor, is effected by normal techniques such as are described in connection with form I.

Through the crystallization, the form II is obtained with a topramezone content of as a rule at least 90% by weight, often at least 94% by weight, in particular at least 96% by weight. The content of form II, based on the total quantity of topramezone is typically at least 90%, often at least 95% and in particular at least 97%.

During the studies on crystalline modifications of topramezone a further form III was also identified. This is in particular a crystalline form of topramezone which at least 90% by weight, in particular at least 95% by weight, consists of the crystalline form Ill.

The form III can be identified by X-ray powder diffractometry on the basis of its diffraction diagram. Thus, an X-ray powder diffractogram recorded at 30° C. using Cu-Kα radiation (1.54178 Å) displays at least 3, often at least 4, in particular at least 5 and especially all of the reflections stated in the following Table 5 as 2θ values, and as interplanar spacings d:

TABLE 5

| 2θ | d [Å] |
|---|---|
| 11.1 ± 0.2 | 8.00 ± 0.05 |
| 12.0 ± 0.2 | 7.36 ± 0.05 |
| 14.5 ± 0.2 | 6.09 ± 0.04 |
| 17.3 ± 0.2 | 5.11 ± 0.03 |
| 17.9 ± 0.2 | 4.94 ± 0.03 |
| 21.9 ± 0.2 | 4.06 ± 0.02 |
| 24.2 ± 0.2 | 3.67 ± 0.02 |

Form III displays a thermogram with a characteristic melting peak. The melting point, determined as the start of the melting peak (onset), typically lies in the range from 223 to 224° C. The latent heat of fusion is about 109 J/g. The values stated here are based on values determined by differential calorimetry (Differential Scanning Calorimetry: DSC, open aluminum crucible, heating rate 10 K/min).

The preparation of the form III of topramezone is effected by crystallization from a solution of topramezone in an aromatic solvent or a $C_5$-$C_8$ ketone at temperatures above 60° C., in particular at temperatures in the range from 90 to 140° C.

Examples of aromatic solvents are benzene, alkylbenzenes such as toluene, xylenes, mesitylene, cumene, etc., chlorobenzene, 1,2-dichlorobenzene, 1,3-dichlorobenzene, 1,4-dichlorobenzene and dichlorobenzene mixtures, anisole and acetophenone. Examples of $C_5$-$C_8$ ketones are acyclic ketones with 5 to 8 carbon atoms such as diethyl ketone (3-pentanone), methyl isobutyl ketone (4-methyl-pentan-2-one) and cyclic ketones with 5 to 8 C atoms such as cyclopentanone, cyclohexanone etc.

For this, in a first step i) a solution of topramezone in the desired solvent is prepared and then in a second step ii) a crystallization of topramezone is effected at temperatures above 80° C., in particular at temperatures in the range from 90 to 150° C. For the dissolution, the mixture of topramezone and the desired solvent will be heated to temperatures above the stated temperatures, and a crystallization then effected at a temperature in this range. It is essential that the crystallization largely proceeds above 80° C.

The crystallization of the form III of topramezone can be effected in the following manner, for example
- by cooling the solution which comprises the dissolved topramezone to a temperature below the temperature used for dissolution, but above 80° C. and in particular in the range from 90 to 150° C.,
- by concentration of the solution which comprises the dissolved topramezone at a temperature above 80° C. and in particular in the range from 90 to 150° C., or
- by a combination of the aforesaid measures.

Preferably the crystallization is effected by concentration at temperatures in the stated temperature range.

The concentration of topramezone in the solution used for the crystallization often lies in the range from 10 to 300 g/l.

Preferably, the solution used for the crystallization of form III comprises topramezone at a purity of at least 85%, often at least 90%, in particular at least 95%, i.e. the content of organic impurities which are not organic solvent makes up not more than 15% by weight, often not more than 10% by weight and in particular not more than 5% by weight, based on the topramezone present dissolved in the solution.

The solution used for the crystallization is preferably essentially free from solvents other than aromatic solvents and $C_5$-$C_8$ ketones. In this context, "essentially free" means that the concentration of solvents including water which are other than aromatic solvents or a $C_5$-$C_8$ ketone in the topramezone-containing solution does not exceed 10% by weight and often 5% by weight, based on the total quantity of solvent.

For the preparation of the solution, essentially any known form of topramezone can be used. Often amorphous topramezone or a mixture of different crystalline modifications or a mixture of amorphous and crystalline topramezone will be used. Also suitable are crystalline forms of topramezone and mixtures thereof, e.g. the form I according to the invention, previously described and the form II, likewise described here, and the forms IV, V-S, VI-S or VII-S not according to the invention, and mixtures of these forms.

The crystallization of form III can be promoted or accelerated by seeding with seed crystals of form III, for example by adding seed crystals of form III before or during the crystallization.

If seed crystals are added during the crystallization, the quantity thereof is typically 0.001 to 10% by weight, often 0.005 to 5% by weight, in particular 0.01 to 1% by weight and especially 0.05 to 0.5% by weight, based on the dissolved topramezone. If the crystallization is carried out in the presence of seed crystals of form III, these are preferably only added at a temperature at which the saturation concentration of topramezone in the solvent in question has been reached, i.e. at or below that temperature at which the dissolved quantity of topramezone in the solvent forms a saturated solution. The temperature dependence of the saturation concentration in a solvent can be determined in routine experiments by the person skilled in the art.

The isolation of the form III from the crystallization product, i.e. the separation of the form III from the mother liquor, is effected by normal techniques such as are described in connection with form I.

Through the crystallization, the form III is obtained with a topramezone content of as a rule at least 90% by weight, often at least 94% by weight, in particular at least 96% by weight. The content of form III, based on the total quantity of topramezone is typically at least 90%, often at least 95% and in particular at least 97%.

Form III can also be generated by controlled cooling of a melt of topramezone. For this, for example the procedure of cooling a melt of topramezone and again heating to a temperature in the range from 110° C. to 160° C. is used. During this, crystallization of the form III takes place. By slow cooling, completion of the crystallization of the form III is then achieved.

In connection with the study of the crystallization of topramezone, two further modifications IV and VIII and solvates of topramezone with toluene (solvate V-S), with chlorobenzene (solvate VI-S) and with dichloromethane (solvate VII-S) were discovered. Compared to formulations which comprise the form I, formulations of these forms, e.g. aqueous suspension concentrates, similarly to formulations of the forms II and III display lower stability.

The form IV can be identified by X-ray powder diffractometry on the basis of its diffraction diagram. Thus, an X-ray powder diffractogram recorded at 30° C. using Cu-Kα radiation (1.54178 Å) displays at least 3, as a rule at least 5, often at least 6, in particular at least 7 and especially all of the reflections stated in the following Table 6 as 2θ values, and as interplanar spacings d:

TABLE 6

| 2θ | d [Å] |
|---|---|
| 5.1 ± 0.2 | 17.34 ± 0.07 |
| 9.3 ± 0.2 | 9.41 ± 0.05 |
| 12.6 ± 0.2 | 7.00 ± 0.05 |
| 14.0 ± 0.2 | 6.34 ± 0.04 |
| 19.1 ± 0.2 | 4.63 ± 0.03 |
| 20.6 ± 0.2 | 4.31 ± 0.03 |
| 21.7 ± 0.2 | 4.10 ± 0.02 |
| 24.6 ± 0.2 | 3.61 ± 0.02 |
| 26.3 ± 0.2 | 3.38 ± 0.01 |

Studies on single crystals of form IV show that the basic crystal structure is monoclinic. The unit cell has the space group P-1. The characteristic data on the crystal structure of form IV (determined at −173° C.) are summarized in Table 7.

TABLE 7

Crystallographic properties of form IV

| Parameter | Form IV |
|---|---|
| Class | monoclinic |
| Space group | P-1 |
| a | 13.9625(5) Å |
| b | 13.9080(5) Å |
| c | 17.796(5) Å |
| α | 90° |
| β | 107.729(5)° |
| γ | 90° |
| Volume | 3292(2) Å$^3$ |
| Z | 4 |
| Density (calculated) | 1.47 g/cm$^3$ |
| R$^1$; ωR$^2$ | 0.13, 0.44 |
| Wavelength | 1.54178 Å | a, b, c = edge length of the unit cell
α, β, γ = angles of the unit cell
Z = number of molecules in the unit cell Form IV displays a thermogram with a characteristic melting peak. The melting point, determined as the start of the melting peak (onset), typically lies in the range from 224 to 225° C. The latent heat of fusion is about 114 to 123 J/g. The values stated here are based on values determined by differential calorimetry (Differential Scanning Calorimetry: DSC, open aluminum crucible, heating rate 10 K/min).

The preparation of the form IV of topramezone is effected by crystallization from a solution of topramezone in a mixture of toluene or benzene with dichloromethane by slow evaporation of the solution at temperatures below 50° C., in particular at temperatures in the range from 10 to 30° C. In the mixture, the volume ratio preferably lies in the range from 2:1 to 1:4.

Crystallization of topramezone by evaporation of a solution of topramezone in a mixture of toluene with dichloromethane in the volume ratio 2:1 at temperatures below 30° C., in particular at temperatures in the range from 10 to 30° C. yields an unstable solvate V-S, which comprises 1 mol of toluene per mol of topramezone. At room temperature, the solvate is already releasing the solvent again and then forms a mixture of the forms II and IV.

Studies on single crystals of the solvate V-S show that the basic crystal structure is monoclinic. The unit cell has the space group P2(1)/c. The characteristic data of the crystal structure of form V-S (determined at 20° C.) are summarized in Table 8.

TABLE 8

Crystallographic properties of the solvate V-S.

| Parameter | Form V-S |
|---|---|
| Class | monoclinic |
| Space group | P2$_1$/c |
| a | 14.052(4) Å |
| b | 15.069(5) Å |
| c | 11.261(3) Å |
| α | 90° |
| β | 106.560(2)° |
| γ | 90° |
| Volume | −2285.7(2) Å$^3$ |
| Z | 4 |
| Density (calculated) | 1.51 g/cm$^3$ |
| R$^1$; ωR$^2$ | 0.084, 0.129 |
| Wavelength | 1.54178 Å | a, b, c = edge length of the unit cell
α, β, γ = angles of the unit cell
Z = number of molecules in the unit cell Crystallization of topramezone by evaporation of a solution of topramezone in a mixture of chlorobenzene with dichloromethane at temperatures below 30° C., in particular at temperatures in the range from 10 to 30° C. yields an unstable solvate VI-S, which comprises 1 mol of chlorobenzene per mol of topramezone. At room temperature, the solvate is already releasing the solvent again and then forms the form II.

Studies on single crystals of the solvate VI-S show that the basic crystal structure is triclinic. The unit cell has the space group P-1. The characteristic data of the crystal structure of form VI-S (determined at −173° C.) are summarized in Table 9.

TABLE 9

Crystallographic properties of the solvate VI-S.

| Parameter | Form VI-S |
|---|---|
| Class | triclinic |
| Space group | P-1 |
| a | 9.3084(8) Å |
| b | 10.2947(9) Å |
| c | 13.2043(9) Å |
| α | 67.473(4)° |
| β | 82.794(5)° |
| γ | 69.685(4) |
| Volume | 1096.0(2) Å$^3$ |
| Z | 2 |
| Density (calculated) | 1.21 g/cm$^3$ |
| R$^1$; ωR$^2$ | 0.062, 0.47 |
| Wavelength | 1.54178 Å | a, b, c = edge length of the unit cell
α, β, γ = angles of the unit cell
Z = number of molecules in the unit cell Crystallization of topramezone by evaporation of a solution of topramezone in dichloromethane at temperatures below 30° C., in particular at temperatures in the range from 10 to 30° C. yields an unstable solvate VII-S, which comprises dichloromethane. At room temperature, the solvate is already releasing the solvent again and then forms the form I.

The solvate VII-S can be identified by X-ray powder diffractometry on the basis of its diffraction diagram. Thus FIG. 5 shows an X-ray powder diffractogram of this sample recorded at 30° C. using Cu-Kα radiation (1.54178 Å).

During the studies on crystalline modifications of topramezone, a further form VIII was also identified. This is in particular a crystalline form of topramezone, which at least 90% by weight, in particular at least 95% by weight, consists of the crystalline form VIII.

The form VIII can be identified by X-ray powder diffractometry on the basis of its diffraction diagram. Thus, an X-ray powder diffractogram recorded at 30° C. using Cu-Kα radiation (1.54178 Å) displays at least 3, often at least 4 in particular at least 5 and especially all of the reflections stated in the following Table 10 as 2θ values, and as interplanar spacings d:

TABLE 10

| 2θ | d [Å] |
|---|---|
| 8.3 ± 0.2 | 11.46 ± 0.07 |
| 16.0 ± 0.2 | 6.52 ± 0.05 |
| 21.4 ± 0.2 | 4.15 ± 0.03 |
| 3.9 ± 0.2 | 22.89 ± 0.02 |
| 25.0 ± 0.2 | 3.56 ± 0.02 |
| 30.6 ± 0.2 | 2.91 ± 0.02 |

Form VIII displays a thermogram with a characteristic melting peak. The melting point, determined as the start of the melting peak (onset), typically lies in the range from 223 to 224° C. The latent heat of fusion is about 115 J/g. The values stated here are based on values determined by differential calorimetry (Differential Scanning Calorimetry: DSC, open aluminum crucible, heating rate 10 K/min).

Like the known amorphous topramezone and other solid forms of topramezone, the form I of topramezone is suitable as a herbicide, however it is superior to these with regard to its ease of handling and of formulation. The invention thus also relates to plant protection agents comprising the crystalline form I and normal additives for the formulation of plant protection agents, in particular plant protection agents in the form of aqueous suspension concentrates (so-called SC's) or non-aqueous suspension concentrates (so-called OD's (oil dispersion or oil-based suspension)), and plant protection agents in the form of water-dispersible powders (so-called WP's) and granules (so-called WG's). The invention also relates to a process for the control of undesired plant growth, wherein plants, the habitat and/or the seeds thereof are subjected to the action of the form I of topramezone, preferably as a suitable active substance preparation.

The plant protection agents which comprise topramezone in the form I control plant growth, in particular monocotyledonous weed species such as *Avena, Lolium, Alopecurus, Phalaris, Echinochloa, Digitaria, Setaria, Cyperus* species, *Agropyron, Cynodon, Imperato* and *Sorghum*, and dicotyledonous weed species such as *Galium, Viola, Veronica, Lamium, Stellaria, Amaranthus, Sinapsis, Ipomoea, Matricaria, Abutilon, Sida, Convolvolus, Cirsium, Rumex* and *Artemisia* very well on non-crop areas, particularly at high application doses. In crops such as wheat, barley, rye, rice, maize, sugar-beet, soya and cotton, they are active against weeds and grass weeds, without appreciably damaging the crop plants. This effect occurs above all with low application doses.

Depending on the particular application method, the form I of topramezone or the plant protection agents comprising it can also be used in a further number of crop plants for the elimination of undesired plants. The following crops are for example possibilities:

*Allium cepa, Ananas comosus, Arachis hypogaea, Asparagus officinalis, Avena sativa Beta vulgaris* spec. *altissima, Beta vulgaris* spec. *rapa, Brassica napus* var. *napus, Brassica napus* var. *napobrassica, Brassica rapa* var. *silvestris, Brassica oleracea, Brassica nigra, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineen-*

*sis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum* (*N. rustica*), *Olea europaea, Oryza sativa, Phaseolus lunatus, Phaseolus vulgaris, Picea abies, Pinus* spec., *Pistacia vera, Pisum sativum, Prunus armeniaca, Prunus avium, Prunus cerasus, Prunus dulcis, Prunus domestica, Prunus persica, Pyrus communis, Ribes sylvestre, Ricinus communis, Saccharum officinarum, Secale cereale, Sinapis alba, Solanum tuberosum, Sorghum bicolor* (*s. vulgare*), *Theobroma cacao, Trifolium pratense, Triticale, Triticum aestivum, Triticum durum, Vicia faba, Vitis vinifera* and *Zea mays.*

In addition, topramezone in the form I or the plant protection agents comprising it can also be used in crops which are tolerant towards the action of herbicides as a result of breeding including genetic engineering methods.

Further, topramezone in the form I or the plant protection agents comprising it can also be used in crops which are tolerant towards insect or fungal attack as a result of breeding including genetic engineering methods.

Like the known amorphous topramezone, the form I of topramezone is also suitable for the defoliation and desiccation of plant parts, for which crop plants such as cotton, potato, rape, sunflower, soya bean or field beans, in particular cotton, are possibilities. In this regard, embodiments of the invention also concern agents for the desiccation and/or defoliation of plants, processes for the preparation of these agents, and processes for the desiccation and/or defoliation of plants using the form I of topramezone.

The form I of topramezone is suitable in particular as desiccant for the drying off of the above-ground parts of crop plants such as potato, rape, sunflower and soya bean, and also cereals. In this way, completely mechanical harvesting of these important crop plants is rendered possible.

Also of economic interest is the facilitation of harvesting which is rendered possible by the time-concentrated drop or reduction of strength of attachment to the tree with citrus fruits, olives or with other species and varieties of pomaceous fruit, drupes and nuts. The same mechanism, i.e. the promotion of the formation of separative tissue between fruit or leaf and shoot part of the plants is also essential for well controllable defoliation of crop plants, in particular cotton.

In addition, the shortening of the time interval in which the individual cotton plants become ripe results in improved fiber quality after the harvest.

Topramezone in the form I or the plant protection agents comprising it can for example be used in the form of powders, suspension, and also high percentage content aqueous, oily or other suspensions, oil suspensions, pastes, dusting agents, scattering agents or granules by spraying, misting, dusting, scattering or pouring. The use forms depend on the use purposes: in every case they should ensure the finest possible distribution of the active substances according to the invention.

The plant protection agents according to the invention comprise topramezone in form I, i.e. at a purity of at least 90% by weight, and additives and/or carriers such as are usual for the formulation of plant protection agents. The quantity of active substance, i.e. the total quantity of topramezone and of other active substances if necessary, in such plant protection agents usually lies in the range from 1 to 98% by weight, in particular in the range from 10 to 95% by weight, based on the total weight of the plant protection agent.

As carriers, in principle all solid and liquid substances which are usually used as carriers in plant protection agents, in particular in herbicide formulations, are possible.

Examples of solid carriers are mineral earths such as silicic acids, silica gels, silicates, talc, kaolin, limestone, lime, chalk, bole, loess, clay, dolomite, diatomaceous earth, calcium and magnesium sulfates, magnesium oxide, ground plastics, fertilizers such as ammonium sulfate, ammonium phosphate, ammonium nitrate, ureas and plant products such as cereal flour, tree bark and wood and nutshell flour, cellulose powder and other solid carriers.

Apart from water, liquid carriers are also organic liquids, e.g. mineral oil fractions of medium to high boiling point such as kerosene and diesel oil, also coal tar oils and oils of plant or animal origin, aliphatic, cyclic and aromatic hydrocarbons, e.g. paraffins, tetrahydronaphthalene, alkylated naphthalenes and derivatives thereof, alkylated benzenes and derivatives thereof, including aromatic and non-aromatic hydrocarbon mixtures, e.g. the products marketed under the trade names Exxsol and Solvesso, alcohols such as propanol, butanol and cyclohexanol, ketones such as cyclohexanone and strongly polar aprotic solvents, e.g. amides such as N-methylpyrrolidone.

Also possible as carriers are the adjuvants typically used for topramezone, which are used alone or in combination with the aforesaid carriers and which are typically selected from penetrants, spreading agents and adhesion promoters. These are substances which usually have a surfactant action. Examples of adjuvants are in particular fatty acid methyl esters, fatty acids, ethoxylated fatty alcohols, ethylene oxide-propylene oxide block copolymers, phosphate and sulfate esters of ethoxylated fatty alcohols, ethoxylated sorbitan fatty acid esters, ethoxylated mono-, di- and triglyceride and the like and mixtures of these products, e.g. the products known under the trade names Dash (BASF), Tween 20 (Uniquema), Hasten (Wilbur-Ellis) and Break-Thru (Degussa-Goldschmidt) and the Lutensol, Pluronic and Plurafac types from the BASF corporation.

Typical auxiliaries comprise surfactant substances, in particular the wetting agents, emulsifiers and dispersant additives normally used in plant protection agents, and also the viscosity-modifying additives (thickeners, thickening agents), antifoaming agents, antifreeze agents, pH adjusting agents, stabilizers, anticaking agents and biocides (preservatives).

Possible surfactant substances are preferably anionic and nonionic surfactants. Suitable surfactant substances are also protective colloids.

The quantity of surfactant substances will as a rule be 0.1 to 60% by weight, in particular 0.5 to 50% by weight, based on the total weight of the plant protection agents according to the invention, or 0.5 to 200% by weight, based on the total quantity of solid active substances in the formulation. Preferably, the surfactant substances comprise at least one anionic surfactant substance and at least one nonionic surfactant substance, wherein the quantity ratio of anionic to nonionic surfactant substance typically lies in the range from 50:1 to 1:50.

Examples of anionic surfactants include alkylarylsulfonates, aromatic sulfonates, e.g. ligninsulfonates (Borresperse types, Borregaard), Kraft lignins (Reax types from MeadWestvaco), oxylignins (Vanillex types from Nippon Paper), phenylsulfonates, naphthalenesulfonates (Morwet types, Akzo Nobel), dibutylnaphthalenesulfonates (Nekal types, BASF), alkyl sulfates, in particular fatty alcohol sulfates, lauryl sulfates, and sulfated hexadeca-, heptadeca- and octadecanols, alkylsulfonates, alkyl ether sulfates, in particular fatty alcohol (poly)glycol ether sulfates, alkylaryl ether sulfates, alkyl polyglycol ether phosphates, polyaryiphenyl ether phosphates, alkylsulfosuccinates, olefin sulfonates, paraffin sulfonates, petroleum sulfonates, taurides, sarcosides, fatty acids, alkylnaphthalenesulfonic acids, naphthalenesulfonic acids, ligninsulfonic acids, polycondensation products of fatty acids, condensation products of sulfonated naphthalenes with formaldehyde, condensation products of sulfonated naphthalenes with formaldehyde and phenol and optionally urea and condensation products of phenolsulfonic acid, formaldehyde and urea, lignin-sulfite waste liquor, alkyl phosphates, alkylaryl phosphates, e.g. tristyryl phosphates, and polycarboxylates such as for example polyacrylates, maleic anhydride/olefin copolymers (e.g. Sokalan® CP9, BASF), including the alkali metal, alkaline earth, ammonium and amine salts of the aforesaid substances. Preferred anionic surfactant substances are those which bear at least one sulfonate group and in particular alkali metal and ammonium salts thereof.

Examples of nonionic surfactant substances are alkylphenol alkoxylates, in particular ethoxylates and ethoxylate co-propoxylates of octylphenol, isooctylphenol, nonylphenol and tributylphenol, di- and tristyrylphenol alkoxylates, alcohol alkoxylates, in particular fatty alcohol ethoxylates and fatty alcohol ethoxylate co-propoxylates, e.g. alkoxylated isotridecanol, fatty amine alkoxylates, polyoxyethylene glycerol fatty acid esters, castor oil alkoxylates, fatty acid alkoxylates, fatty acid amide alkoxylates, fatty acid polydiethanolamides, lanolin ethoxylates, fatty acid polyglycol esters, isotridecyl alcohol, ethoxylated fatty acid amides, ethoxylated fatty acid esters, alkylpolyglycosides, ethoxylated alkylpolyglycosides, sorbitan fatty acid esters, ethoxylated sorbitan fatty acid esters, glycerol fatty acid esters, lower molecular weight polyalkylene oxides such as polyethylene glycol, polypropylene oxide, polyethylene oxide co-polypropylene oxide di- and triblock copolymers, and mixtures thereof. Preferred nonionic surfactant substances are fatty alcohol ethoxylates, alkylpolyglycosides, glycerol fatty acid esters, castor oil ethoxylates, fatty acid ethoxylates, fatty acid amide ethoxylates, lanolin ethoxylates, fatty acid polyglycol esters, ethylene oxide-propylene oxide block copolymers and mixtures thereof.

Protective colloids are typically water-soluble, amphiphilic polymers, which in contrast to the aforesaid surfactants typically have molecular weights over 2000 Daltons (number average). Examples of these are proteins and denatured proteins such as casein, polysaccharides such as water-soluble starch derivatives and cellulose derivatives, hydrophobically modified starches and celluloses, e.g. methylcellulose, and also polycarboxylates such as polyacrylic acid, acrylic acid copolymers and maleic acid copolymers (BASF Sokalan types), polyvinyl alcohol (Mowiol types from Clariant), polyalkoxylates, polyvinylpyrrolidone, vinylpyrrolidone copolymers, polyvinylamines, polyethylenimines (Lupasol types from BASF), and higher molecular weight polyalkylene oxides such as polyethylene glycol, polypropylene oxides and polyethylene oxide co-polypropylene oxide di- and triblock copolymers.

The plant protection agents according to the invention can also comprise one or more viscosity-modifying additives (thickeners). This is understood in particular to mean substances and substance mixtures, which impart a modified flow behavior to the formulation, e.g. a high viscosity in the resting state and low viscosity in the agitated state. The nature of the thickener depends on the nature of the formulation. As examples of thickeners may be mentioned: inorganic substances, e.g. layer silicates and organically modified layer silicates such as bentonite or attapulgite (e.g. Attaclay®, Engelhardt), and organic substances such as polysaccharides and heteropolysaccharides such as Xanthan Gum® (Kelzan® from Kelco), Rhodopol® 23 (Rhone Poulenc) or Veegum® (R. T. Vanderbilt). The quantity of the viscosity-modifying additives is often 0.1 to 5% by weight, based on the total weight of the plant protection agent.

Examples of antifoaming agents are the silicone emulsions well known for this purpose (Silikon® SRE, Wacker or Rhodorsil® from Rhodia), long-chain alcohols, fatty acids and salts thereof, defoamants of the aqueous wax dispersion type, solid defoamants (so-called Compounds), organofluorine compounds and mixtures thereof. The quantity of antifoamant is typically 0.1 to 1% by weight, based on the total weight of the plant protection agent.

For stabilization, preservatives can also be added to the plant protection agents according to the invention. Suitable preservatives are those based on isothiazolones, for example Proxel® from ICI or Acticide® RS from Thor Chemie or Kathon® MK from Rohm & Haas. The quantity of preservative is typically 0.05 to 0.5% by weight, based on the total weight of the SC.

Aqueous plant protection agents, i.e. those with an aqueous carrier, often comprise antifreeze agents. Suitable antifreeze agents are liquid polyols, e.g. ethylene glycol, propylene glycol or glycerine and also urea. The quantity of antifreeze agents is as a rule 1 to 20% by weight, in particular 5 to 10% by weight, based on the total weight of the aqueous plant protection agent.

If the plant protection agents comprising the crystalline modification I, II or III are used for seed treatment, they can comprise other usual components, such as are used in seed treatment, for example in dressing or coating. As well as the aforesaid components, these in particular include colorants, adhesives, fillers and plasticizers.

As colorants, all the normal dyes and pigments for such purposes are possible. Here both pigments of low solubility in water and also water-soluble dyes are usable. As examples, the dyes and pigments known under the names Rhodamin B, C. I. Pigment Red 112 and C. I. Solvent Red 1, Pigment Blue 15:4, Pigment Blue 15:3, Pigment Blue 15:2, Pigment Blue 15:1, Pigment Blue 80, Pigment Yellow 1, Pigment Yellow 13, Pigment Red 48:2, Pigment Red 48:1, Pigment Red 57:1, Pigment Red 53:1, Pigment Orange 43, Pigment Orange 34, Pigment Orange 5, Pigment Green 36, Pigment Green 7, Pigment White 6, Pigment Brown 25, Basic Violet 10, Basic Violet 49, Acid Red 51, Acid Red 52, Acid Red 14, Acid Blue 9, Acid Yellow 23, Basic Red 10 and Basic Red 108 may be mentioned. The quantity of colorant will normally make up not more than 20% by weight of the formulation and preferably lies in the range from 0.1 to 15% by weight, based on the total weight of the formulation.

As adhesives, all usual binders usable in dressing agents are possible. Examples of suitable binders comprise thermoplastic polymers such as polyvinylpyrrolidone, polyvinyl acetate, polyvinyl alcohol and tylose and also polyacrylates, polymethacrylates, polybutenes, polyisobutenes, polystyrene, polyethylene amines, polyethylene amides, the aforesaid protective colloids, polyesters, polyether esters, polyanhydrides, polyester urethanes, polyester amides, thermoplastic polysaccharides, e.g. cellulose derivatives such as cellulose esters, cellulose ethers, cellulose ether esters, including methylcellulose, ethylcellullose, hydroxymethylcellulose, carboxymethylcellulose, hydroxypropylcellulose and starch derivatives and modified starches, dextrins, maltodextrins, alginates and chitosans, and also fats, oils, proteins, including casein, gelatin and zein, gum Arabic and shellac. The adhesives are preferably plant-compatible, i.e. they display no or no significant phytotoxic effects. The adhesives are preferably biologically degradable. The adhesive is preferably is selected such that it acts as a matrix for the active components of the formulation. The quantity of adhesive will usually make up not more than 40% by weight of the formulation and preferably lies in the range from 1 to 40% by weight and in particular in the range from 5 to 30% by weight, based on the total weight of the formulation.

In addition to the adhesive, the formulation for seed treatment can also comprise inert fillers. Examples of these are the aforesaid solid carrier materials, in particular finely divided inorganic materials such as clays, chalk, bentonite, kaolin, talc, perlite, mica, silica gel, diatomaceous earth, quartz powder and montmorillonite, but also finely divided organic materials such as wood flour, cereal flour, activated charcoal and the like. The quantity of filler is preferably selected such that the total quantity of filler does not exceed 70% by weight, based on the total weight of all non-volatile components of the formulation. Often the quantity of filler lies in the range from 1 to 50% by weight, based on the total weight of all non-volatile components of the formulation.

In addition the formulation for the seed treatment can also comprise a plasticiser which increases the flexibility of the coating. Examples of plasticisers are oligomeric polyalkylene glycols, glycerin, dialkyl phthalates, alkyl benzyl phthalates, glycol benzoates and comparable compounds. The quantity of plasticiser in the coating often lies in the range from 0.1 to 20% by weight, based on the total weight of all non-volatile components of the formulation.

A preferred embodiment of the invention relates to liquid formulations of form I. In addition to the solid active substance phase, these have at least one liquid phase, in which topramezone is present in the form I in the form of dispersed fine particles.

Possible liquid phases are water and those organic solvents in which the form I has only slight or zero solubility, e.g. those in which the solubility of form I at 25° C. and 1013 mbar is not more than 1% by weight, in particular not more than 0.1% by weight and especially not more than 0.01% by weight.

According to a first preferred embodiment, the liquid phase is water and aqueous solvent, i.e. solvent mixtures which in addition to water also comprise up to 20% by weight, preferably however not more than 10% by weight, based on the total quantity of water and solvent, of one or more organic solvents miscible with water, e.g. water-miscible ethers such as tetrahydrofuran, methylglycol, methyldiglycol, alkanols such as isopropanol or polyols such as glycol, glycerin, diethylene glycol, propylene glycol and the like. Such formulations are also hereinafter referred to suspension concentrates (SC's).

Such suspension concentrates comprise topramezone as form I, as form II or as form III in a finely divided particulate form, wherein the particles of form I, form II or form III are present suspended in an aqueous phase. The size of the active substance particles, i.e. the size, which 90% by weight of the active substance particles do not exceed, here typically lies below 30 µm, in particular below 20 µm. Advantageously, in the SC's according to the invention at least 40% by weight, in particular at least 60% by weight and especially at least 80% by weight of the particles have diameters below 2 µm.

The quantity of active substance, i.e. the total quantity of topramezone and of any other active substances if applicable, in such SC's usually lies in the range from 10 to 70% by weight, in particular in the range from 20 to 50% by weight, based on the total weight of the suspension concentrate.

In addition to the active substance, aqueous suspension concentrates typically comprise surfactant substances, and if appropriate antifoaming agents, thickeners, antifreeze agents, stabilizers (biocides), pH-adjusting agents and anticaking agents.

Aqueous formulations typically have a pH value<8, in particular <6.

As surfactant substances, the previously mentioned surfactant substances are possible. Preferably the aqueous plant protection agents according to the invention comprise at least one of the previously mentioned anionic surfactants and if appropriate one or more nonionic surfactants, if appropriate in combination with a protective colloid. The quantity of surfactant substances will as a rule amount to 1 to 50% by weight, in particular 2 to 40% by weight, based on the total weight of the aqueous SC's according to the invention. Preferably, the surfactant substances comprise at least one anionic surfactant substance and at least one nonionic surfactant substance, where the quantity ratio of anionic to nonionic surfactant substance typically lies in the range from 50:1 to 1:50.

Concerning the nature and quantity of the antifoaming agents, thickeners, antifreeze agents and biocides, the aforesaid applies.

If appropriate, the SC's according to the invention can comprise aqueous buffers for pH regulation. Examples of buffers are alkali metal salts of weak inorganic or organic acids such as for example phosphoric acid, boric acid, acetic acid, propionic acid, citric acid, fumaric acid, tartaric acid, oxalic acid and succinic acid.

According to another preferred embodiment, the liquid phase consists of non-aqueous organic solvents, wherein the solubility of form I of topramezone at 25° C. and 1013 mbar is not more than 1% by weight, in particular not more than 0.1% by weight and especially not more than 0.01% by weight. These include in particular aliphatic and alicyclic hydrocarbons and oils, in particular those of plant origin, and also $C_1$-$C_4$ alkyl esters of saturated or unsaturated fatty acids or fatty acid mixtures, in particular the methyl esters, e.g. oleic acid methyl ester, stearic acid methyl ester, rape oil methyl ester, but also paraffinic mineral oils and the like. Accordingly, the present invention also relates to agents for plant protection in the form of a non-aqueous suspension concentrate, which is hereinafter also referred to as OD (oil-dispersion). Such OD's comprise the form I of topramezone in a finely divided particulate form, wherein the particles of form I are present suspended in a non-aqueous phase. The size of the active substance particles, i.e. the size which 90% by weight of active substance particles do not exceed, here typically lies below 30 µm, in particular below 20 µm. Advantageously, in the non-aqueous suspension concentrates at least 40% by weight, in particular at least 60% by weight and especially at least 80% by weight of the particles have diameters below 2 µm.

The quantity of active substance, i.e. the total quantity of topramezone and of any other active substances, in such OD's usually lies in the range from 10 to 70% by weight, in particular in the range from 20 to 50% by weight, based on the total weight of the non-aqueous suspension concentrate.

In addition to the active substance and the liquid carrier, non-aqueous suspension concentrates comprise typically surfactant substances, and if appropriate antifoaming agents, agents for modifying the rheological properties and stabilizers (biocides).

Possible surfactant substances are preferably the previously mentioned anionic and nonionic surfactants. The quantity of surfactant substances will as a rule amount to 1 to 40% by weight, in particular 2 to 30% by weight, based on the total weight of the non-aqueous SC's according to the invention. Preferably the the surfactant substances comprise at least one anionic surfactant substance and at least one nonionic surfactant substance, where the quantity ratio of anionic to nonionic surfactant substance typically lies in the range from 20:1 to 1:20.

The form I of topramezone according to the invention can also be formulated as a solid plant protection agent. These include powder, scattering and dusting agents but also water-dispersible powders and granules, e.g. coated, impregnated and homogeneous granules. Such formulations can be produced by mixing or grinding together form I of topramezone with a solid carrier and if necessary further additives, in particular surfactant substances. Granules can be produced by binding of the active substances to solid carriers. Solid carriers are mineral earths such as silicic acids, silica gels, silicates, talc, kaolin, limestone, lime, chalk, bole, loess, clay, dolomite, diatomaceous earth, calcium and magnesium sulfate, magnesium oxide, ground plastics, fertilizers such as ammonium sulfate, ammonium phosphate, ammonium nitrate, ureas and plant products such as cereal flour, tree bark-, wood- and nutshell flour, cellulose powder or other solid carriers. Solid formulations can also be produced by spray-drying, if appropriate in the presence of polymeric or inorganic drying aids and if appropriate in the presence of solid carriers. For the preparation of solid formulations of topramezon of form I, extrusion processes, fluidized bed granulation, spray granulation and comparable technologies are also suitable.

As possible surfactant substances, the previously mentioned anionic surfactants and protective colloids are preferable. The quantity of surfactant substances will as a rule be 1 to 30% by weight, in particular 2 to 20% by weight, based on the total weight of the solid formulation according to the invention.

The quantity of active substance, i.e. the total quantity of topramezone and of other active substances if necessary, in such solid formulations typically lies in the range from 10 to 70% by weight, in particular in the range from 20 to 50% by weight, based on the total weight of the non-aqueous suspension concentrate.

The following formulation examples illustrate the production of such preparations:

I. Water-Dispersible Powder:
  20 parts by weight of form I are mixed well with 3 parts by weight of the sodium salt of diisobutylnaphthalenesulfonic acid, 17 parts by weight of the sodium salt of a ligninsulfonic acid from a sulfite waste liquor and 60 parts by weight of powdered silicic acid gel and ground in a hammer-mill. In this way, a water-dispersible powder which comprises the form I is obtained.

II. Dusting Agent:
  5 parts by weight of form I are mixed with 95 parts by weight of finely divided kaolin. In this way, a dusting agent which comprises 5% by weight of form I is obtained.

III. Non-Aqueous Suspension Concentrate:
  20 parts by weight of form I are intimately mixed with 2 parts by weight of the calcium salt of dodecylbenzenesulfonic acid, 8 parts by weight of fatty alcohol polyglycol ether, 2 parts by weight of the sodium salt of a phenolsulfonic acid-urea-formaldehyde condensation product and 68 parts by weight of a paraffinic mineral oil, e.g. by grinding together or by the action of strong shear forces. A stable suspension concentrate of form I is obtained.

IV. Non-Aqueous Suspension Concentrate:
  20 parts by weight of form I are ground to a fine active substance suspension with the addition of 10 parts by weight of dispersant and wetting agents and 70 parts by weight of a paraffinic mineral oil in an attrition mill. A stable non-aqueous suspension concentrate of form I is obtained. On dilution in water, a stable suspension of the active substance is obtained. The active substance content in the formulation is 20% by weight.

V. Aqueous Suspension Concentrate:
  10 parts by weight of form I are formulated as an aqueous suspension concentrate in a solution of 17 parts by weight of a poly(ethylene glycol)-(propylene glycol) block copolymer, 2 parts by weight of a phenolsulfonic acid-formaldehyde condensation product and about 1 part by weight of other additives (thickeners, defoamants) in a mixture of 7 parts by weight of propylene glycol and 63 parts by weight of water.

VI. Aqueous Suspension Concentrate:
  20 parts by weight of form I are ground to a fine active substance suspension with the addition of 10 parts by weight of dispersant and wetting agents and 70 parts by weight of water in an attrition mill. On dilution in water, a stable suspension of the active substance is obtained. The active substance content in the formulation is 20% by weight.

VII. Water-Dispersible and Water-Soluble Granules
  50 parts by weight of form I are finely ground with the addition of 50 parts by weight of dispersant and wetting agents formulated as water-dispersible or water-soluble granules by means of industrial devices (e.g. extrusion, spraying tower, fluidized bed). On dilution in water, a stable dispersion or solution of the active substance is obtained. The formulation has an active substance content of 50% by weight.

VIII. Water-Dispersible and Water-Soluble Powders
  75 parts by weight of form I are ground in a rotor-stator mill with the addition of 25 parts by weight of dispersant and wetting agents and also silicic acid gel. On dilution in water, a stable dispersion or solution of the active substance is obtained. The active substance content of the formulation is 75% by weight.

IX. Gel Formulations
  In a ball mill, 20 parts by weight of form I, 10 parts by weight of dispersant, 1 part by weight of gelling agent and 70 parts by weight of water or an organic solvent are ground to a fine suspension. On dilution with water, a stable suspension is obtained. The active substance content of the formulation is 20% by weight.

X: Directly Applicable Granules (GR, FG, GG, MG)
  0.5 parts by weight of form I are finely ground and bonded with 99.5 parts by weight of carriers. Common processes for this are extrusion, spray drying or fluidized bed. As a result, granules for direct application with a 0.5% by weight active substance content are obtained.

The application of form I or of the herbicidal agents comprising it, if the formulation is not already ready to use, is effected in the form of aqueous sprays. These are prepared by dilution of the aforesaid form I-containing formulations with water. The sprays can also comprise further components in dissolved, emulsified or suspended form, for example fertilizers, active substances of other herbicidal or growth-regulating active substance groups, other active substances, e.g. active substances for the control of animal pests or phytopathogenic fungi or bacteria, and also mineral salts which are used for the elimination of nutrient and trace element deficiencies, and non-phytotoxic oils and oil concentrates. As a rule, these components are added to the spray before, during or after the dilution of the formulations according to the invention.

The application of form I or of the plant protection agents comprising it can be effected in pre-emergence or post-emergence procedures. Insofar as topramezone is less tolerable for certain crop plants, application techniques can be used wherein the herbicidal agents are sprayed using the spray equipment in such a manner that the leaves of the sensitive crop plants are as far as possible not contacted, while the active substances reach the leaves of undesired plants growing thereunder or the uncovered earth surface (post-directed, lay-by).

The quantities of topramezone used, depending on control target, season, target plants and growth stage, are 0.001 to 3.0, preferably 0.01 to 1.0 kg/ha active substance (a. s.).

In a further embodiment, the application of form I or the plant protection agents comprising it can be effected by the treatment of seed.

Treatment of seed essentially comprises all techniques familiar to the person skilled in the art (seed dressing, seed coating, seed dusting, seed soaking, seed film coating, seed multilayer coating, seed encrusting, seed dripping, and seed pelleting) on the basis of topramezone in form I or agents prepared therefrom. For this, the plant protection agents can be applied diluted or undiluted.

The term seed comprises seed of all kinds, such as for example grains, seeds, fruit, tubers, cuttings and similar forms. Preferably, the term seed here describes grains and seeds.

As the seed, seed of the previously mentioned useful plants but also the seed of transgenic plants or of plants obtained by conventional breeding methods can be used.

For the seed treatment, topramezone is normally used in quantities of 0.001 to 10 kg per 100 kg of seed.

To broaden the spectrum of activity and to achieve synergistic effects, the forms I can be mixed and applied together with many members of other herbicidal or growth-regulating active substance groups. In addition, it can be advantageous to formulate or apply topramezone together with safeners.

For example, possible mixing partners are 1,2,4-thiadiazoles, 1,3,4-thia-diazoles, amides, aminophosphoric acid and derivatives thereof, amino-triazoles, anilides, aryloxy-/heteroaryloxyalkanoic acids and derivatives thereof, benzoic acid and derivatives thereof, benzothiadiazinones, 2-(hetaroyl/aroyl)-1,3-cyclohexanediones, heteroaryl aryl ketones, benzyl-isoxazolidinones, meta-$CF_3$-phenyl derivatives, carbamates, quinoline-carboxylic acid and derivatives thereof, chloroacetanilides, cyclohexenone oxime ether derivatives, diazines, dichloropropionic acid and derivatives thereof, dihydrobenzofurans, dihydrofuran-3-ones, dinitroanilines, dinitrophenols, diphenyl ethers, dipyridyls, halocarboxylic acids and derivatives thereof, ureas, 3-phenyluracils, imidazoles, imidazolinones, N-phenyl-3,4,5,6-tetrahydrophthalimides, oxadiazoles, oxiranes, phenols, aryloxy- and heteroaryloxyphenoxypropionic acid esters, phenylacetic acid and derivatives thereof, 2-phenylpropionic acid and derivatives thereof, pyrazoles, phenylpyrazoles, pyridazines, pyridinecarboxylic acid and derivatives thereof, pyrimidyl ethers, sulfonamides, sulfonylureas, triazines, triazinones, triazolinones, triazolecarboxamides, uracils and phenylpyrazolines and isoxazolines and derivatives thereof. Particularly suibable as mixing partners are coherbicides such as terbuthylazin, bromoxynil, the sodium salt thereof and esters thereof with $C_4$-$C_8$ carboxylic acids, dicamba, S-metolachlor or pethoxamid, and safeners such as isoxadifen.

In addition it can be useful to apply the form I alone or jointly in combination with other herbicides also further mixed with other plant protection agents, for example with agents for the control of pests or phytopathogenic fungi or bacterial. Also of interest is its miscibility with mineral salt solutions which are used for the elimination of nutritional and trace element deficiencies. Additives such as non-phytotoxic oils and oil concentrates can also be added.

The following figures and examples serve to illustrate the invention and should not be interpreted as limiting.

The melting points were determined by DSC with a Mettler Toledo DSC 25 from Mettler with a heating rate of 10 K/min in the range from 25° to +140° C. The sample size was 5 to 10 mg.

Preparation of Form I of Topramezone

EXAMPLE 1

Figure 1:
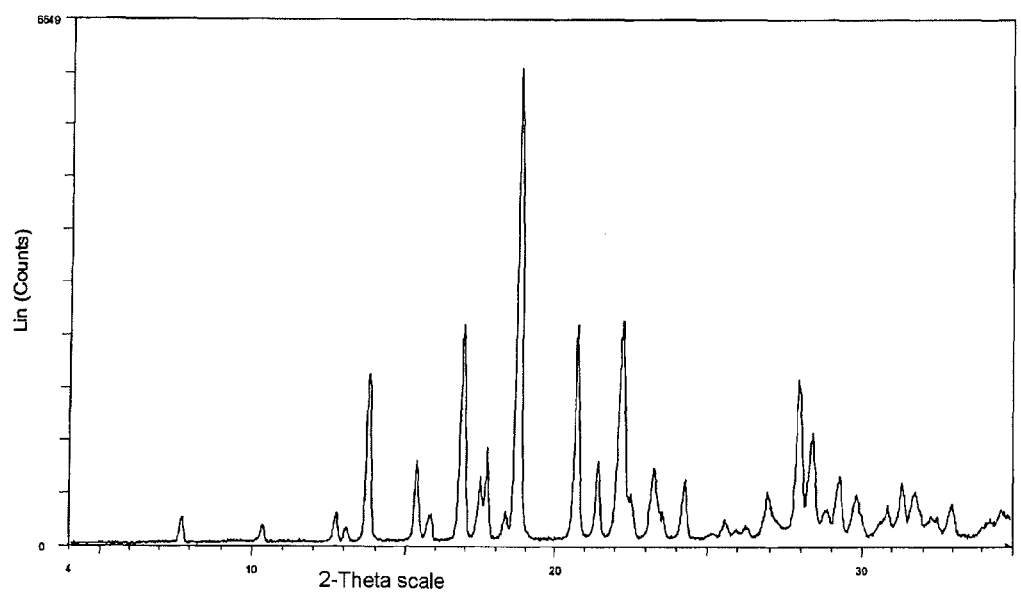
FIG. 1 shows an X-ray powder diffractogram of form I. The X-ray powder diffractogram of form I was recorded with a Bruker-AXS D-5000 diffractometer in reflection geometry in the range from $2\theta=2°-40°$ with a step width of $0.02°$ using Cu-$K_\alpha$ radiation (1.54178 Å) at 25 or 30° C.

In a sample container, 1 g of topramezone of 96% purity was dissolved in 40 ml of acetone at about 30° C. The solution was filtered and the filtrate was then concentrated at a temperature of about 30° C. by passing a current of nitrogen over the liquid surface. After 2 days, the experiment was ended, and the crystallization product obtained was separated, dried and analyzed. The crystallization yield was over 80%. The crystalline product had a melting point of 218° C. The crystallization product exhibited the X-ray powder diffractogram shown in FIG. 1.

EXAMPLE 2

The experiment was performed analogously to Example 1, ethanol being used as the solvent instead of acetone. The crystalline product had a melting point of 218° C. An X-ray powder diffractogram confirmed the presence of form I.

EXAMPLE 3

The experiment was performed analogously to Example 1, isopropanol being used as the solvent instead of acetone. The crystalline product had a melting point of 217° C. An X-ray powder diffractogram confirmed the presence of form I.

EXAMPLE 4

In a sample container, 1 g of topramezone of 96% purity was dissolved in 40 ml of acetone under reflux. The hot solution was filtered and again heated to reflux. The filtrate was then cooled to about 25° at 5 to 10 K/min. Next it was concentrated by passing a current of nitrogen over the liquid surface. The crystallization product obtained was separated, dried and analyzed. The crystalline product had a melting point of 220° C. An X-ray powder diffractogram confirmed the presence of form I.

EXAMPLE 5

In a sample container, 1 g of crystalline topramezone of form IV with a purity of 96% was suspended for 7 days with stirring in 20 ml of a mixture of 9 parts by volume of isopropanol and 1 part by volume of water. The supernatant was then removed by centrifugation. After drying overnight on an earthenware plate, a crystalline material with a melting point of 220° C. was obtained. An X-ray powder diffractogram confirmed the presence of form I.

EXAMPLE 6

The experiment was performed analogously to Example 5, methanol being used instead of isopropanol as the solvent component. The crystalline product had a melting point of 219° C. An X-ray powder diffractogram confirmed the presence of form I.

EXAMPLE 7

In a sample container, 1.4 g of crystalline topramezone in the form of a 1:1 mixture of forms II and III (purity>96%) was suspended in 20 ml of a mixture of 1 part by volume of methanol and 9 parts by volume of water with stirring for 7 days. The supernatant was then removed by centrifugation. After drying overnight, a crystalline material with a melting point of 220° C. was obtained. An X-ray powder diffractogram confirmed the presence of form I.

EXAMPLE 8

The experiment was performed analogously to Example 7, ethylene glycol being used instead of von methanol as the solvent component. The crystalline product had a melting point of 220° C. An X-ray powder diffractogram confirmed the presence of form I.

EXAMPLE 9

The experiment was performed analogously to Example 7, topramezone as pure form II being used instead of the mixture of form II and form III. The crystalline product had a melting point of 219° C. An X-ray powder diffractogram confirmed the presence of form I.

EXAMPLE 10

In a flask, 1.6 g of topramezone of 96% purity was dissolved in 110 ml of methanol under reflux and the hot solution was filtered. This was then concentrated on the rotary evaporator at a pressure of 65 to 86 mbar and a bath temperature of about 35° C. The crystalline product thus obtained had a melting point of 218° C. An X-ray powder diffractogram confirmed the presence of form I.

EXAMPLE 11

The experiment was performed analogously to Example 10, isopropanol being used instead of methanol as a solvent component. The crystalline product had a melting point of 217° C. An X-ray powder diffractogram confirmed the presence of form I.

EXAMPLE 12

In a pressure vessel, 318 g of 3-(3-bromo-2-methyl-6-methylsulfonylphenyl)-4,5-dihydroisoxazole were dissolved in 2565 g of dioxan and 98 g of 1-methyl-5-hydroxy-pyrazole, 10.5 g of triphenylphosphine, 346 g of potassium carbonate and 0.345 g of palladium(II) chloride were added to this with stirring. This was flushed 3 times with CO, heated to 130° C. and the CO pressure was then increased to 15 bar. The mixture was then stirred for 25 hrs at 130° C. and a pressure of 15 bar with continuous further addition of CO.

The reaction mixture was then poured into about 4400 g of water, undissolved matter was filtered off and dioxan/water distilled off to give a final volume of about 2500 ml. About 1800 g of methanol were added to this, and the product was precipitated at 60° C. by addition of 430 g of concentrated hydrochloric acid. The suspension was cooled to 20 ° C. and the solid was filtered off and the solid was then washed with water. Next the solid was suspended in 1920 g of methanol and heated for 8 hrs under reflux. Next the mixture was cooled to 20° C. within 4 hrs then stirred for a further 2 hrs at 20° C. The solid was separated from the mother liquor by filtration and then washed 3 times with methanol. The crystalline solid this obtained had a melting point of 220° C. An X-ray powder diffractogram confirmed the presence of form I.

Preparation of Form II of Topramezone

EXAMPLE 13

Figure 2:
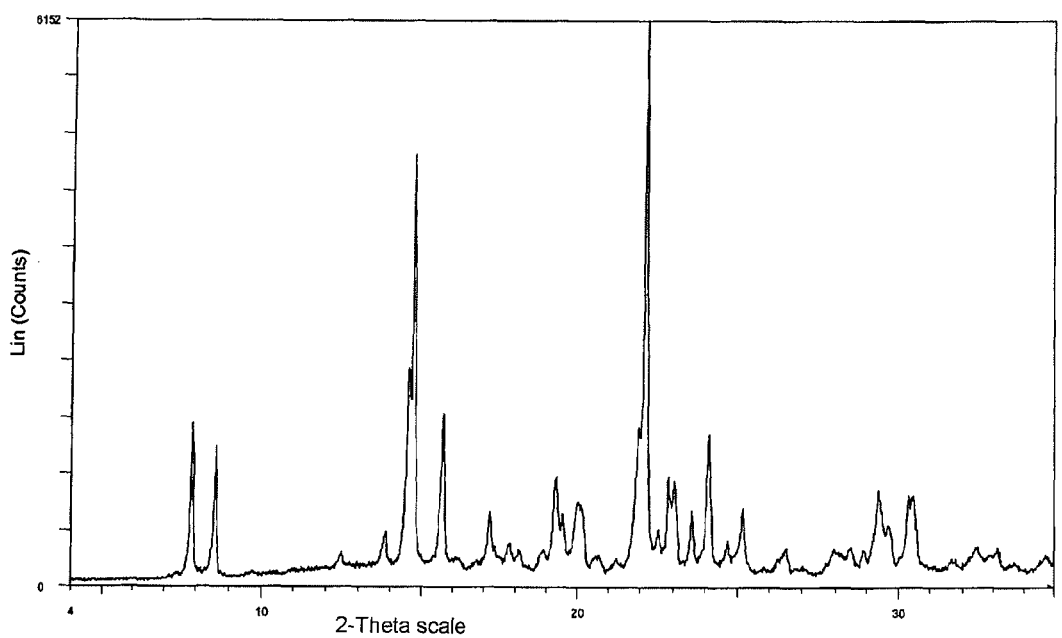
FIG. 2 shows an X-ray powder diffractogram of form II. The X-ray powder diffractogram was recorded under the conditions stated for FIG. 1.

In a sample container, 1 g of topramezone of 96% purity was dissolved in 60 ml of toluene under reflux. The solution was cooled to 20° C., filtered and the filtrate then evaporated to dryness at a temperature of about 30° C. by passing a current of nitrogen over the liquid surface. The crystallization product obtained was separated and analyzed. The crystalline product had a melting point of 222 to 223° C. The crystallization product exhibited the X-ray powder diffractogram of form II shown in FIG. 2.

EXAMPLE 14

The experiment was performed analogously to Example 13, 1,2-dichlorobenzene being used as the solvent instead of toluene. The crystalline product had a melting point of 222° C. An X-ray powder diffractogram confirmed the presence of form II.

EXAMPLE 15

The experiment was performed analogously to Example 13, methyl isobutyl ketone being used as the solvent instead of toluene. The crystalline product had a melting point of 222° C. An X-ray powder diffractogram confirmed the presence of form II.

Preparation of Form III of Topramezone

EXAMPLE 16

Figure 3:
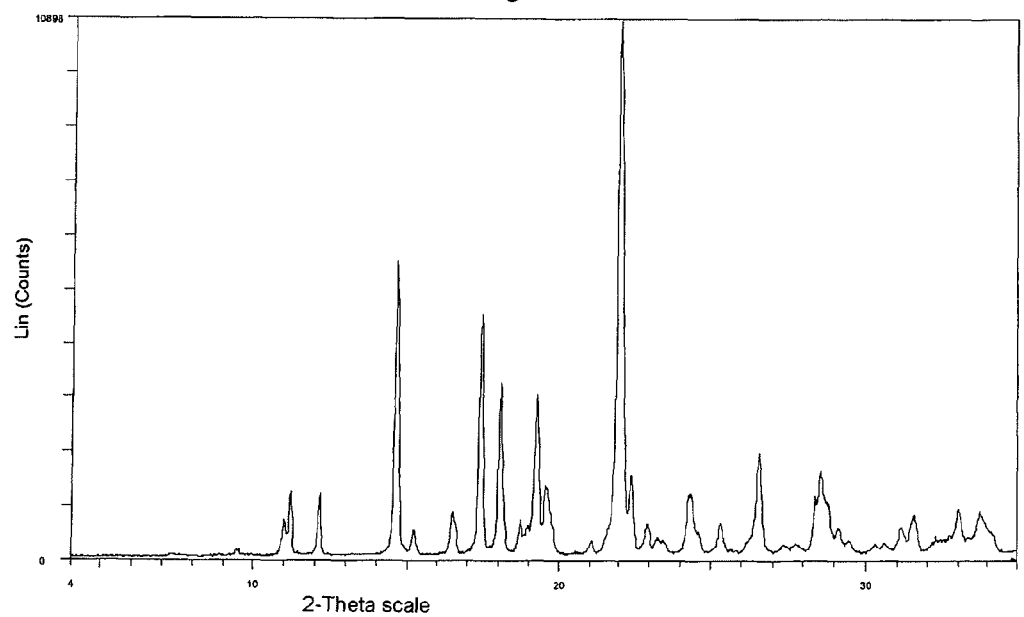
FIG. 3 shows an X-ray powder diffractogram of form III. The X-ray powder diffractogram was recorded under the conditions stated for FIG. 1.
Figure 4:
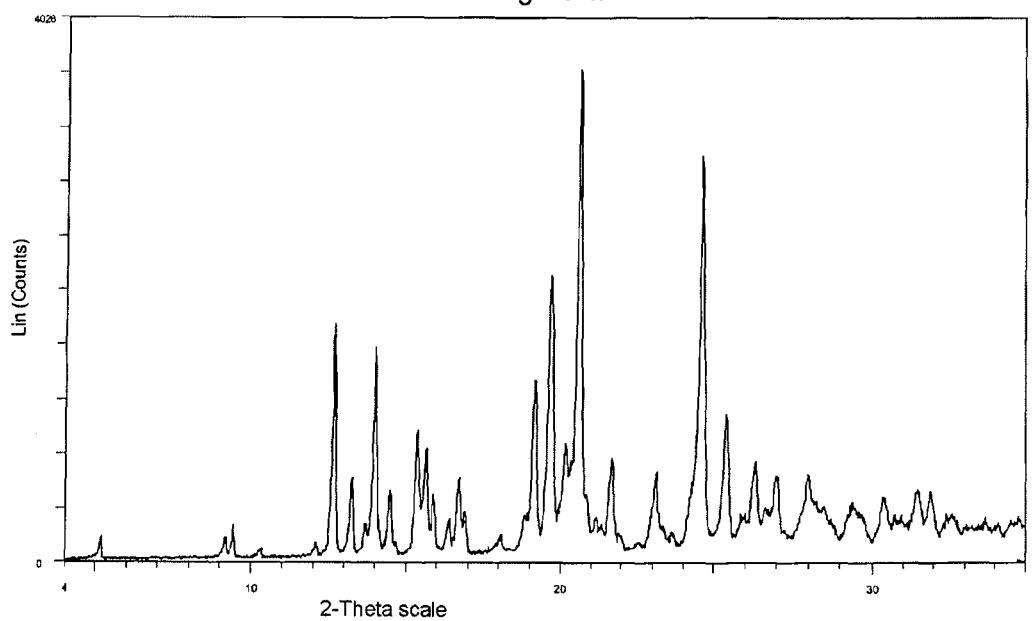
FIG. 4 shows an X-ray powder diffractogram of form IV. The X-ray powder diffractogram was recorded under the conditions stated for FIG. 1.
Figure 5:
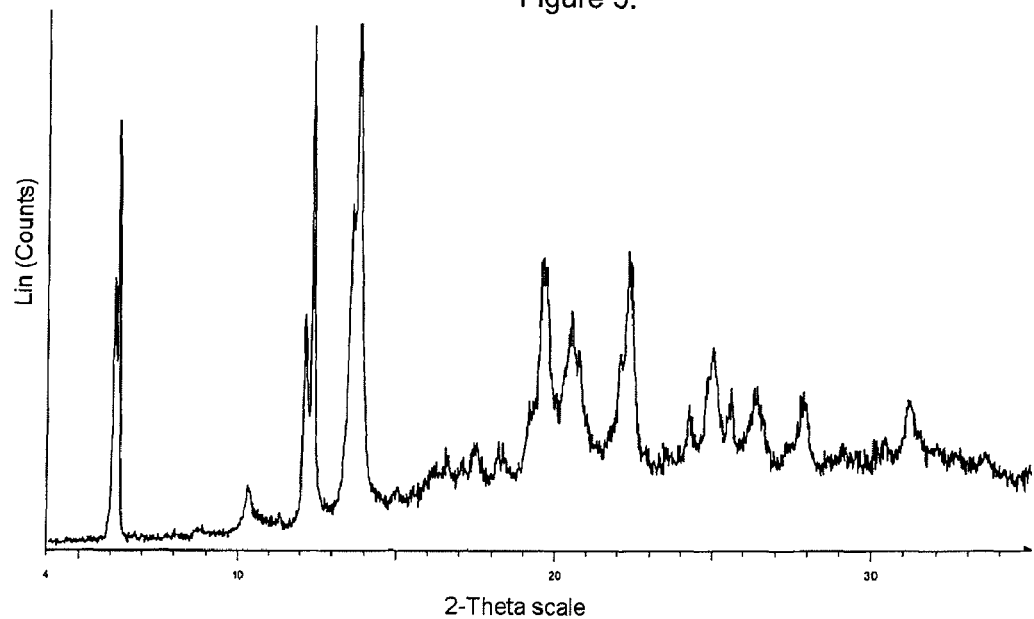
FIG. 5 shows an X-ray powder diffractogram of the solvate VII-S. The X-ray powder diffractogram was recorded under the conditions stated for FIG. 1.
Figure 6:
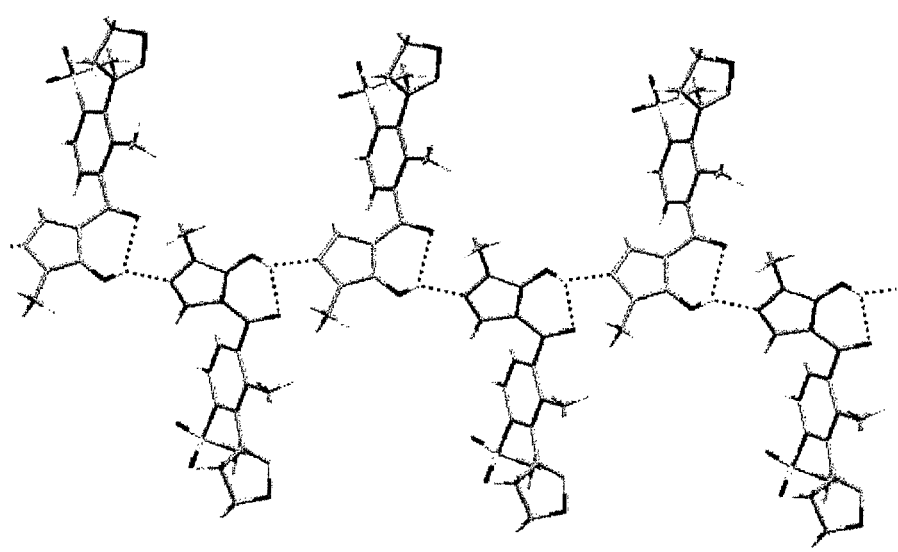
FIG. 6 shows the orientation of the topramezone molecules in the crystal lattice of form I. Hydrogen bridge bonds are shown as dotted lines.
Figure 7:
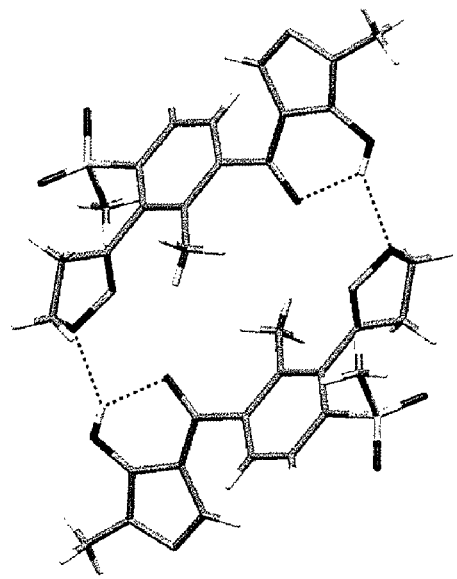
FIG. 7 shows the orientation of the topramezone molecules in the crystal lattice of form II. Hydrogen bridge bonds are shown as dotted lines.
Figure 8:
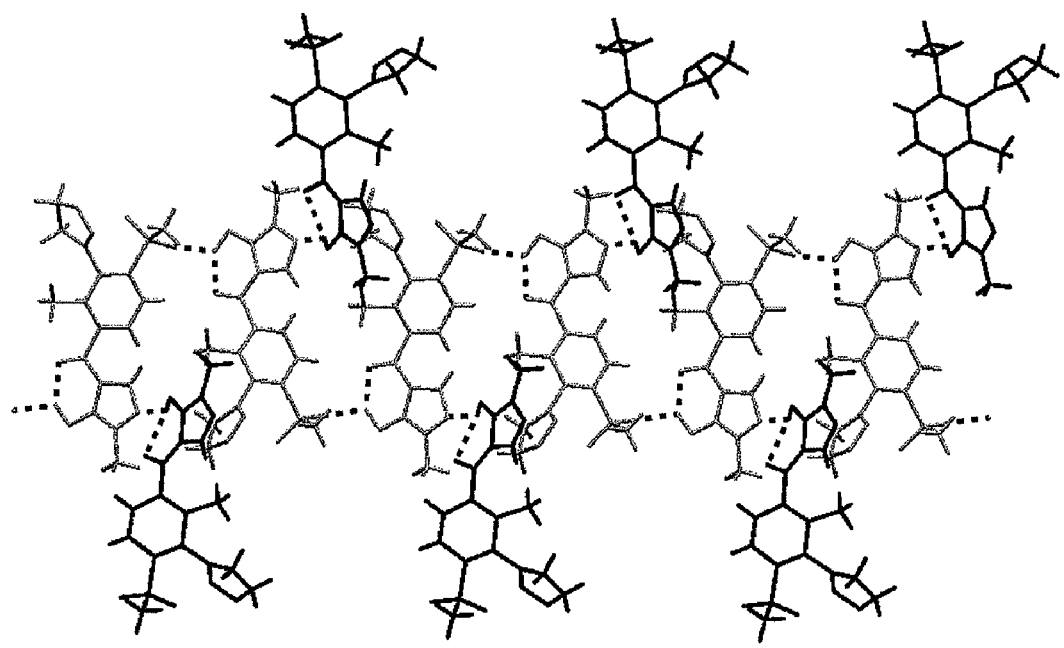
FIG. 8 shows the orientation of the topramezone molecules in the crystal lattice of form IV. Hydrogen bridge bonds are shown as dotted lines.
Figure 9:
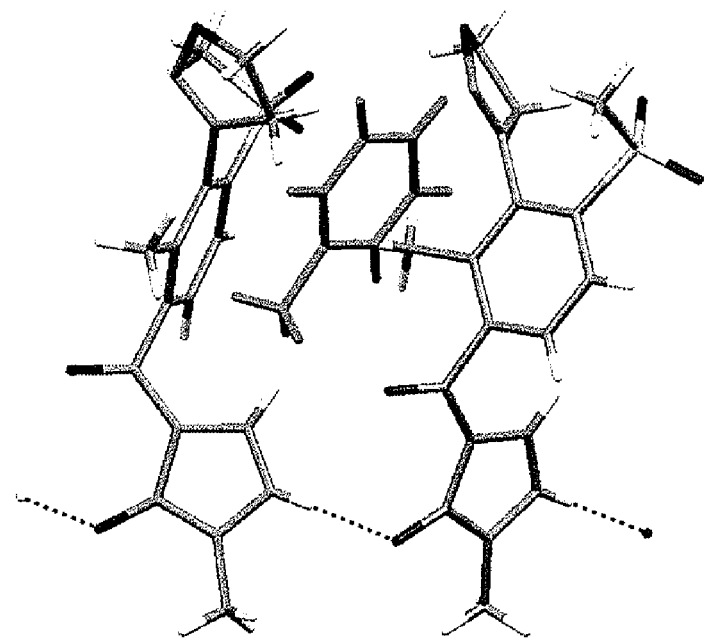
FIG. 9 shows the orientation of the topramezone molecules and the toluene in the crystal lattice of the solvate V-S. Hydrogen bridge bonds are shown as dotted lines.
Figure 10:
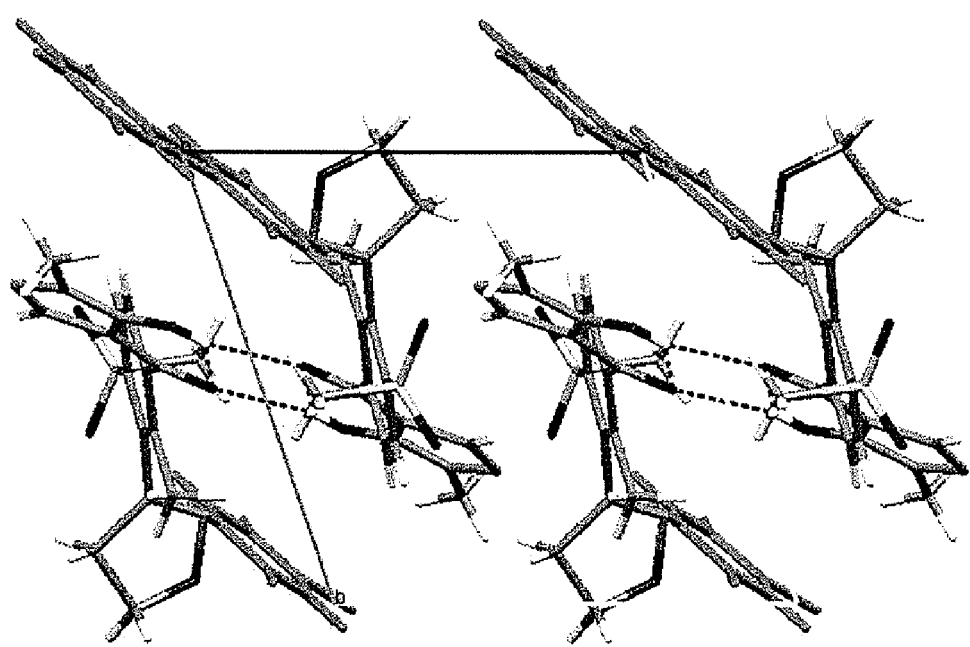
FIG. 10 shows the orientation of the topramezone molecules and the chlorobenzene in the crystal lattice of the solvate VI-S. Hydrogen bridge bonds are shown as dotted lines (view along the c-axis of the unit cell).
Figure 11:
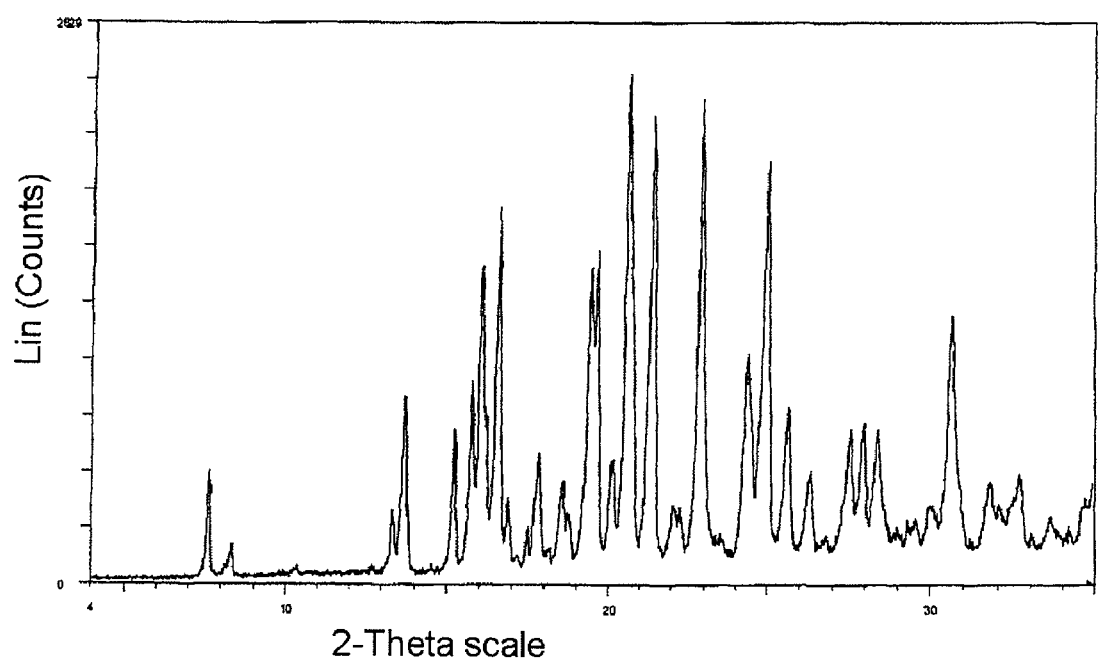
FIG. 11 shows an X-ray powder diffractogram of form VIII. The X-ray powder diffractogram was recorded under the conditions stated for FIG. 1.

In a sample container, 1 g of topramezone of 96% purity was dissolved in 20 ml of acetophenone under reflux. The hot solution was filtered and the filtrate then evaporated to dryness at a temperature of about 100° C. by passing a current of nitrogen over the liquid surface. The crystallization product obtained was separated, dried and analyzed. The crystalline product had a melting point of 222° C. The crystallization product exhibited the X-ray powder diffractogram of form III shown in FIG. 3.

EXAMPLE 17

The experiment was performed analogously to Example 16, 1,2-dichlorobenzene being used instead of acetophenone as the solvent. The crystalline product had a melting point of 223° C. An X-ray powder diffractogram confirmed the presence of form III.

EXAMPLE 18

The experiment was performed analogously to Example 16, diethyl ketone being used instead of acetophenone as the solvent. The crystalline product had a melting point of 222° C. An X-ray powder diffractogram confirmed the presence of form III.

Preparation of a Formulation
  Materials Used:
    Emulsifier 1: EO/PO triblock copolymer with a molecular weight of 6500 and a propylene oxide content of 50% by weight.
    Emulsifier 2: sodium salt of a phenolsulfonic acid-formaldehyde condensation—product
    Thickener: xanthan gum
    Defoamer: normal commercial polydimethylsiloxane filler emulsion (Wacker Silikon SRE-PFL) (active substance content 20% by weight)
    Microbiocide: formulation comprising mixture of 1,2-benzisothiazolin-3-one and 2-methyl-4-isothiazolin-3-one, active substance content 5% by weight (Aktizide MBS from Thor Chemie GmbH).

EXAMPLE 19

Aqueous Suspension Concentrate of Topramezone of Form I 1. 400 g of demineralized water were placed in a stirrer vessel and 60 g of 1,2-propylene glycol, 20 g of emulsifier 2 and 166.7 g of an 18% by weight aqueous solution of emulsifier 1 were successively added to this. It was stirred until a homogeneous, clear solution was obtained and 343.9 g of crystalline topramezone of form I with a topramezone content >98% and 1 g of defoamant were then successively added to this. The suspension thus obtained was cooled to about 15° C. and it was then passed through a rotor-stator mill and then through a ball mill with cooling, until the desired particle size distribution was attained. In this way, an aqueous topramezone suspension was obtained, wherein 80% by weight of the particles exhibited a diameter below 2 μm.

2. 10 g of 1,2-propylene glycol and 119.4 g of demineralized water were placed in a stirrer vessel, and then 3 g of thickener and then 2 g of the microbiocide were successively added with stirring. Next, the solution thus obtained was added with stirring to the suspension obtained in step 1, and after this a further 4 g of the defoamant were added thereto with stirring. In this way, an aqueous suspension was obtained which comprised about 336 g/l of topramezone in form I and exhibited a viscosity, determined in accordance with OECD 114, of about 60 to 100 mPa·s. The particle size distribution was characterized by a $d_{90}$ value of $\leq 3.5$ μm and a $d_{50}$ value of $\leq 1.3$ μm.

EXAMPLE 20

Preparation of a Suspoemulsion Concentrate Comprising Topramezone of Form I and Dimethenamid-P 44.4 g of 1,2-propylene glycol, 44.4 g of emulsifier 2 and 66.6 g of a 2% by weight aqueous solution of the thickener which comprised 1.6% by weight of the biocide were added with stirring to 285.7 g of demineralized water. 561 g of Dimethenamid P were added to this solution with stirring at 23° C. and the mixture was stirred until a stable emulsion was obtained. 107.6 g of the suspension concentrate prepared in Example 19 were then added to the emulsion thus obtained and it was stirred for a further 10 minutes.

In this manner, an aqueous suspoemulsion which had a Dimethenamid-P content of about 538 g and a content of topramezone in form I of about 32 g/l was obtained. The density was about 1.11 g/cm³. The viscosity, determined with a rotation viscosimeter in accordance with OECD Test Procedure 114 was about 70 to 90 mPa·s. The $d_{90}$ value was below 7 μm and the $d_{50}$ value was below 1.5 μm. The pH of an approximately 1% by weight dilution in demineralized water was in the range from about 2.5 to 4.5.

The invention claimed is:

1. A crystalline form I of [3-(4,5-dihydro-3-isoxazolyl)-2-methyl-4-(methylsulfonyl)phenyl]-(5-hydroxy-1-methyl-1H-pyrazol-4-yl)methanone, which in an X-ray powder diffractogram at 30° C. with Cu-Kα radiation displays at least 5 of the following reflections, stated as 2θ values: 7.7±0.2°, 10.3±0.2°, 12.7±0.2°, 13.8±0.2°, 16.9±0.2°, 18.8±0.2°, 20.7±0.2°, 22.2±0.2°, 28.0±0.2° and 31.4±0.2°.

2. [3-(4,5-dihydro-3-isoxazolyl)-2-methyl-4-(methylsulfonyl)phenyl]-(5-hydroxy-1-methyl-1H-pyrazol-4-yl)methanone, being composed of at least 90% by weight of the crystalline form I of claim 1.

3. A process for the preparation of the crystalline form I according to claim 1, comprising:
  i) preparing a solution of [3-(4,5-dihydro-3-isoxazolyl)-2-methyl-4-(methylsulfonyl)phenyl]-(5-hydroxy-1-methyl-1H-pyrazol-4-yl)methanone in a polar organic solvent, which is selected from the group consisting of $C_1$-$C_4$ alkanols, $C_2$-$C_4$ alkanediols, acetone and the mixture thereof with water, and
  ii) performing a crystallization of [3-(4,5-dihydro-3-isoxazolyl)-2-methyl-4-(methylsulfonyl)phenyl]-(5-hydroxy-1-methyl-1H-pyrazol-4-yl)methanone to prepare crystalline form I.

4. A process for the preparation of the crystalline form I according to claim 1, comprising:

i) preparing a suspension of [3-(4,5-dihydro-3-isoxazolyl)-2-methyl-4-(methylsulfonyl)phenyl]-(5-hydroxy-1-methyl-1H-pyrazol-4-yl)methanone in a polar organic solvent, which is selected from $C_1$-$C_4$ alkanols, $C_2$-$C_4$ alkanediols, acetone and a mixture thereof with water, and ii) stirring the suspended material in the suspension to prepare crystalline form I.

5. A plant protection agent, comprising [3-(4,5-dihydro-3-isoxazolyl)-2-methyl-4-(methylsulfonyl)phenyl]-(5-hydroxy-1-methyl-1H-pyrazol-4-yl)methanone, which is composed of at least 90% by weight of the crystalline form I according to claim 1, and one or more additives conventional for the formulation of plant protection agents.

6. The plant protection agent according to claim 5 in the form of an aqueous suspension concentrate.

7. The plant protection agent according to claim 5 in the form of a non-aqueous suspension concentrate.

8. The plant protection agent according to claim 5 in the form of a powder or granule dispersible in water.

9. A method for the control of undesired plant growth, comprising subjecting plants, the habitat and/or the seeds thereof to the action of [3-(4,5-dihydro-3-isoxazolyl)-2-methyl-4-(methylsulfonyl)-phenyl]-(5-hydroxy-1-methyl-1H-pyrazol-4-yl)methanone, which is composed of at least 90% by weight of the crystalline form I according to claim 1.

* * * * *